United States Patent
Palepu et al.

(10) Patent No.: US 11,103,483 B2
(45) Date of Patent: *Aug. 31, 2021

(54) FORMULATIONS OF BENDAMUSTINE

(71) Applicant: Eagle Pharmaceuticals, Inc., Woodcliff Lake, NJ (US)

(72) Inventors: Nagesh R. Palepu, Southampton, PA (US); Philip Christopher Buxton, Uxbridge (GB)

(73) Assignee: Eagle Pharmaceuticals, Inc., Woodcliff Lake, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/509,920

(22) Filed: Jul. 12, 2019

(65) Prior Publication Data
US 2019/0350904 A1   Nov. 21, 2019

Related U.S. Application Data

(63) Continuation of application No. 16/015,656, filed on Jun. 22, 2018, now abandoned, which is a continuation of application No. 15/432,335, filed on Feb. 14, 2017, now Pat. No. 10,010,533, which is a continuation of application No. 15/013,436, filed on Feb. 2, 2016, now Pat. No. 9,572,797, which is a continuation of application No. 14/031,879, filed on Sep. 19, 2013, now Pat. No. 9,265,831, which is a continuation of application No. 13/016,473, filed on Jan. 28, 2011, now Pat. No. 8,609,707.

(60) Provisional application No. 61/299,100, filed on Jan. 28, 2010.

(51) Int. Cl.
| | | |
|---|---|---|
| A61K 9/08 | (2006.01) | |
| A61P 35/00 | (2006.01) | |
| A61K 31/4184 | (2006.01) | |
| A61K 47/10 | (2017.01) | |
| A61K 47/20 | (2006.01) | |
| A61K 47/12 | (2006.01) | |
| A61K 47/18 | (2017.01) | |
| A61K 47/22 | (2006.01) | |
| A61K 9/00 | (2006.01) | |

(52) U.S. Cl.
CPC ............ *A61K 31/4184* (2013.01); *A61K 9/08* (2013.01); *A61K 47/10* (2013.01); *A61K 47/12* (2013.01); *A61K 47/18* (2013.01); *A61K 47/20* (2013.01); *A61K 47/22* (2013.01); *A61K 9/0019* (2013.01)

(58) Field of Classification Search
CPC .... A61K 31/4184; A61K 47/10; A61K 47/12; A61K 47/18; A61K 47/186; A61K 47/20; A61K 47/22; A61K 9/0019; A61K 9/08
See application file for complete search history.

(56) References Cited

U.S. PATENT DOCUMENTS

| | | | |
|---|---|---|---|
| 4,071,620 A | 1/1978 | Sklar | |
| 4,711,906 A * | 12/1987 | von Stetten | A61K 47/10 514/561 |
| 4,879,286 A | 11/1989 | Alam | |
| 5,204,335 A | 4/1993 | Sauerbier | |
| 5,223,515 A | 6/1993 | Mikura | |
| 5,741,523 A | 4/1998 | Teagarden | |
| 7,252,799 B2 * | 8/2007 | Miekka | A61L 2/0058 422/22 |
| 7,772,274 B1 | 8/2010 | Palepu | |
| 8,076,366 B2 | 12/2011 | Courvoisier | |
| 8,344,006 B2 | 1/2013 | Drager | |
| 8,389,558 B2 | 3/2013 | Alakhov | |
| 8,609,707 B2 * | 12/2013 | Palepu | A61K 47/22 514/394 |
| 8,791,270 B2 | 7/2014 | Brittain | |
| 9,000,021 B2 | 4/2015 | Sundaram | |
| 9,034,908 B2 * | 5/2015 | Sundaram | A61K 31/4184 514/394 |
| 9,144,568 B1 * | 9/2015 | Sundaram | A61K 47/22 |
| 9,265,831 B2 * | 2/2016 | Palepu | A61K 47/18 |
| 9,572,796 B2 * | 2/2017 | Palepu | A61K 9/08 |
| 9,572,797 B2 * | 2/2017 | Palepu | A61K 47/12 |
| 9,572,887 B2 * | 2/2017 | Sundaram | A61K 47/20 |
| 9,572,888 B2 | 2/2017 | Sundaram | |

(Continued)

FOREIGN PATENT DOCUMENTS

| | | |
|---|---|---|
| CN | 1850048 A | 10/2006 |
| CN | 101584668 | 11/2009 |

(Continued)

OTHER PUBLICATIONS

Treanda (Highlights of prescribing information 2008) (Year: 2008).*
Rowe et al. ("Rowe", Handbook of Pharmaceutical Excipients, 6th edition, 2009, pp. 454-455) (Year: 2009).*
Qin et al. (Chem Commun. 2009;5112-5114). (Year: 2009).*
Hsu et al. Reactions of N-Ethyl-(HN-1), N-Methyl-Bis(2-Chloroethyl)Amine (HN-2), and Tris(2-Chloroethyl)Amine (HN-3) With Peroxides; 2002; 13 pages. (Year: 2002).*
Jones, C.W. Applications of Hydrogen Peroxide and Derivatives 1999 Royal Society of Chemistry). (Year: 1999).*
Waterman et al. (2002) Stabilization of Pharmaceuticals to Oxidative Degradation, Pharmaceutical Development and Technology, 7:1, 1-32, DOI: 10.1081/PDT-120002237). (Year: 2002).*

(Continued)

*Primary Examiner* — Ernst V Arnold
(74) *Attorney, Agent, or Firm* — BakerHostetler

(57) ABSTRACT

Long term storage stable bendamustine-containing compositions are disclosed. The compositions can include bendamustine or a pharmaceutically acceptable salt thereof, and a pharmaceutically acceptable fluid which can include in some embodiments PEG, PG or mixtures thereof and an antioxidant or chloride ion source. The bendamustine-containing compositions have less than about 5% total impurities, on a normalized peak area response ("PAR") basis as determined by high performance liquid chromatography ("HPLC") at a wavelength of 223 nm, after at least about 15 months of storage at a temperature of from about 5° C. to about 25° C.

16 Claims, No Drawings

(56) References Cited

U.S. PATENT DOCUMENTS

| | | | |
|---|---|---|---|
| 9,579,384 B2 | 2/2017 | Sundaram | |
| 9,597,397 B2* | 3/2017 | Sundaram | A61K 47/22 |
| 9,597,398 B2 | 3/2017 | Sundaram | |
| 9,597,399 B2* | 3/2017 | Sundaram | A61K 47/22 |
| 10,010,533 B2* | 7/2018 | Palepu | A61K 9/08 |
| 2002/0102215 A1 | 8/2002 | Klaveness | |
| 2002/0122768 A1 | 9/2002 | Liu | |
| 2004/0014964 A1 | 1/2004 | Cheesman | |
| 2004/0043069 A1 | 3/2004 | Vanderbist | |
| 2005/0025702 A1 | 2/2005 | Decicco | |
| 2005/0042285 A1 | 2/2005 | Ukai | |
| 2006/0035945 A1 | 2/2006 | Attardo | |
| 2006/0128777 A1 | 6/2006 | Bendall | |
| 2006/0159713 A1* | 7/2006 | Brittain | A61P 35/00 424/400 |
| 2006/0205694 A1 | 9/2006 | Alonso | |
| 2007/0116729 A1 | 5/2007 | Palepu | |
| 2008/0118544 A1 | 5/2008 | Wang | |
| 2009/0082416 A1 | 3/2009 | Czarnik | |
| 2009/0209606 A1 | 8/2009 | Bendall | |
| 2009/0264488 A1 | 10/2009 | Cooper | |
| 2009/0325978 A1 | 12/2009 | Onai | |
| 2010/0092474 A1 | 4/2010 | Gallagher | |
| 2010/0145266 A1 | 6/2010 | Orlowski | |
| 2010/0216858 A1 | 8/2010 | Popek | |
| 2010/0247669 A1 | 9/2010 | Eliasof | |
| 2010/0273730 A1 | 10/2010 | Hsu | |
| 2011/0015244 A1 | 1/2011 | Alakhov | |
| 2011/0015245 A1 | 1/2011 | Alakhov | |
| 2011/0184036 A1 | 7/2011 | Palepu | |
| 2011/0190363 A1 | 8/2011 | Drager | |
| 2012/0059000 A1 | 3/2012 | Ren | |
| 2012/0071532 A1 | 3/2012 | Cooper | |
| 2012/0157505 A1 | 6/2012 | Labell | |
| 2012/0308516 A1 | 12/2012 | Hlavinka | |
| 2013/0041003 A1 | 2/2013 | Brittain | |
| 2013/0041004 A1 | 2/2013 | Drager | |
| 2013/0210878 A1 | 8/2013 | Soppimath | |
| 2013/0210879 A1 | 8/2013 | Palepu | |
| 2013/0217888 A1 | 8/2013 | Shrawat | |
| 2013/0253025 A1 | 9/2013 | Sundaram | |
| 2014/0094496 A1 | 4/2014 | Sundaram | |
| 2014/0275196 A1 | 9/2014 | Sundaram | |
| 2018/0000789 A1 | 1/2018 | Palepu | |
| 2018/0000938 A1 | 1/2018 | Sundaram | |
| 2018/0185488 A1 | 7/2018 | Sundaram | |
| 2018/0296535 A1 | 10/2018 | Palepu | |
| 2018/0296536 A1 | 10/2018 | Palepu | |
| 2018/0369383 A1 | 12/2018 | Sundaram | |
| 2019/0192659 A1 | 6/2019 | Sundaram | |

FOREIGN PATENT DOCUMENTS

| | | |
|---|---|---|
| CN | 102164579 | 8/2011 |
| DE | 80967 | 1/1970 |
| DE | 159289 | 3/1983 |
| JP | H09508128 | 8/1997 |
| JP | 2005537285 | 12/2005 |
| JP | 2008526991 | 7/2008 |
| JP | 2012503666 | 2/2012 |
| JP | 2012525387 | 10/2012 |
| JP | 2015501814 | 1/2015 |
| WO | 9901118 | 1/1999 |
| WO | 2001097860 | 12/2001 |
| WO | 2001097861 | 12/2001 |
| WO | 2001098294 | 12/2001 |
| WO | 0202125 | 1/2002 |
| WO | 2006054315 | 5/2006 |
| WO | 2006110551 | 10/2006 |
| WO | 2010036702 | 4/2010 |
| WO | 2010126676 | 11/2010 |
| WO | 2010148288 | 12/2010 |
| WO | 2011094565 | 8/2011 |
| WO | 2011103150 A2 | 8/2011 |
| WO | 2012015810 | 2/2012 |
| WO | 2013142358 | 9/2013 |

OTHER PUBLICATIONS

Amin et al. (Journal of Pharmaceutical Sciences 2004;93(9):2244-2249). (Year: 2004).*

Ni et al. (international Journal of Pharmaceutics 2001;226:39-46) (Year: 2001).*

"Ready-to-use" [online] retrieved on May 27, 2021 from: https://medical-dictionary.thefreedictionary.com/ready-to-use; 1 page). (Year: 2021).*

Sigma-Aldrich, Webpage Catalog for poly(ethylen glycol), http://www.sigmaaldrich.com/catalog/product/aldrich/202398?lang=en®ion-=US#, accessed Nov. 15, 2015 (2 pages).

Sikora, "Cancer drug development in the post-genomic age," Current Science, vol. 81 No. 5 pp. 549-554 (2001).

Spectra Analysis, Inc., "Oxidative Degradation of Polyethyleneglycol (PEG) studied by LC-IR", Application Note 016, Mar. 2008.

Spiegel et al., "Use of Nonaqueous Solvents in Parenteral Products," Journal of Pharmaceutical Sciences, vol. 52, No. 10 pp. 917-927 (1963).

Strickley, Solubilizing Excipients in Oral and Injectable Formulations, Pharmaceutical Research 21(2):201-230 (Feb. 2004).

Supplemental European Search Report issued in connection with PCT/US2011/022958 dated Dec. 16, 2013.

T. W. Graham Solomons, Organic Chemistry (John Wiley & Sons, 3d ed. 1984).

Tageja, Bendamustine: Safety and Efficacy in the Management of Indolent Non-Hodgkins Lymphoma, Clinical Medicine Insights: Oncology 2011:5 145-156.

Teagarden & Baker, Practical Aspects of Freeze-Drying of Pharmaceutical and Biological Products Using Non-Aqueous Co-Solvent Systems, Chapter 8 in Freeze-Drying/Lyophilization of Pharmaceutical and Biological Products, 239-76 (2nd Edition, Edited by Rey, L. & May, J., Marcel Dekker, New York) (2004).

Teagarden & Baker, Practical Aspects of Lyophilization Using Non-Aqueous Co-Solvent Systems, 15 Eur. J. Pharma. Sciences, 115-33 (2002).

Thiesen, "Bendamustine, a well-tollerated cytotoxic agent used in Germany for may years, is soon to be marketed in the rest of Europe for a range of indicatons including chronic lymphocytic leukaemia," pp. 1-4 (2010).

Third Party Submission in related EP2528602 based on PCT/US2011/022958 dated Nov. 19, 2013 (9 pages).

Thomas A. Jennings, Lyophilization, Introduction and Basic Principles (2006)(original copyright 1999).

Treanda, "Highlights of Prescribing Information," Treanda ( bendamustine hydrochloride) for Injection, for intravenous infusion, pp. 1-13 (2010).

Treanda, "Highlights of Prescribing Information," Treanda ( bendamustine hydrochloride) for Injection, for intravenous infusion, pp. 1-6 (2008).

USP 24/NF 19 (2000) entry for Propylene Glycol (USP).

V.G. Vinogradova, et al., Polymer Yearbook 13, New Metal Chelates as Antioxidant Stabilizers for Polymers . . . , pp. 87-111, 1996.

V.M. Mikhal'chuk, et al., Antioxidative Stabilization of Polyethylene . . . , Russian Journal of Applied Chemistry, vol. 77, No. 1, pp. 131-135, 2004.

Vlok, Manual of Nursing, vol. 1 (9th edition), 1988.

W. Fürst, et al., "About the Hydrolytic Decomposition of IMET 3393," Pharmazeutische Zentralhalle, vol. 108, Issue 9, pp. 608-614, 1969 (English translation and the original article).

Wayne P. Olson, Volatile Solvents for Drying and Microbial Kill in the Final Container, Pharmaceutical Engineering, 110-118 (1997).

Weide et al., Bendamustine Mitoxantrome and Rituximab (BMR): A New Effective Regimen for Refractory or Relapsed Indolent Lymphomas, Leukemia & Lymphoma, 43(2):327-331 (2002).

Werner et al., Hydrolysis Products of Cancerostatic Cytostasan® (Bendamustine), 42 (4) Die Pharmazie, Govi Verlag Pharmazeutischer Verlag GMBH, Eschborn, DE, 272-73.

(56) References Cited

OTHER PUBLICATIONS

William H. Brown, Organic Chemistry 5th Edition, pp. 358-360, 2009.
Wittaya-Areekul and Nail, Freeze-Drying of tert-Butyl Alcohol/Water Cosolvent Systems: Effects of Formulation and Process Variables on Residual Solvents, Journal of Pharmaceutical Sciences 87(4):491-495 (1998).
Written Opinion issued in counterpart PCT/US2013/032289 dated Jun. 6, 2013.
Written Opinion issued in counterpart PCT/US2013/032295 dated Jun. 3, 2013.
Zimmerman et al., Elements of Organic Chemistry (1977).
Zips et al., "New Anticancer Agents: In Vitro and In Vivo Evaluation," In Vivo,vol. 19 pp. 1-8 (2005).
Zumdahl et al., Chemistry, 7th Ed. (2007).
Pokorny et al., Antioxidants in Food: Practical Applications 2001 CRC Press p. 324 (2004).
Cyclobond® Handbook, A Guide to Using Cyclodextrin Bonded Phases for Chiral LC Separations, 6th ed., 2002, Advanced Separation Technologies, Inc., pp. 1-58, pp. 42-45.
Armstrong et al., Separation of Drug Stereoisomers by the Formation of . . . beta-Cyclodextrin Inclusion Complexes, Science, vol. 232, pp. 1132-1135, May 30, 1986.
*Cerhalon, Inc, et al. v. Slayback Pharma Limited Liability Company*—Civil Action No. 1:17-cv-01154: Complaint (Document 1), dated Aug. 16, 2017.
*Cephalon, Inc., et al., v. Slayback Pharma Limited Liability Company*—Civil Action No. 1:17-cv-00154: Defendant Slayback Pharma Limited Liability Company's Answer to Complaint and Counterclaims (Document 11), dated Sep. 29, 2017.
*Cephalon, Inc., et al., v. Slayback Pharma Limited Liability Company, et al.*—Civil Action No. 1: 17-cv-01154: Answer to Slayback Pharma Limited Liability Company's Counterclaims, dated Oct. 20, 2017.
*Cephalon, Inc., et al., v. Slayback Pharma Limited Liability Company, et al.*—Civil Action No. 1:17-cv-01154: Answer to Apotex Inc. and Apotex Corp.'s Counterclaims (Document 22), dated Dec. 18, 2017.
*Cephalon, Inc., et al., v. Slayback Pharma Limited Liability Company, et al.*—Civil Action No. 1:17-cv-01154: Answer to Slayback Pharma Limited Liability Company's Counterclaims (Document 56), dated Mar. 5, 2018.
*Cephalon, Inc., et al., v. Slayback Pharma Limited Liability Company, et al.*—Civil Action No. 1:17-cv-01154: Joint Claim Construction Chart (Document 94), dated Jul. 24, 2018.
*Cephalon, Inc., et al., v. Slayback Pharma Limited Liability Company*—Civil Action No. 1:17-cv-01154: Joint Status Report (Document 164), dated Oct. 19, 2018.
*Teva Pharmaceuticals International GMBH, et al. v. Apotex Inc., et al.*—Civil Action No. 1:17-cv-01164: Complaint (Document 1), dated Aug. 18, 2017.
*Teva Pharmaceuticals International GMBH, et al. v. Apotex Inc., et al.*—Civil Action 1:17-cv-01164: Defendants Apotex Inc. and Apotex Corp.'s Answer to Complaint, Defenses and Counterclaims (Document 17), dated Nov. 27, 2017.
*Teva Pharmaceuticals International GMBH, et al. v. Fresenius Kabi USA, LLC.*—Civil Action No. 1:17-cv-01201: Complaint (Document 1), dated Aug. 24, 2017.
*Teva Pharmaceuticals International GMBH, et al. v. Fresenius Kabi USA, LLC.*—Civil Action No. 1:17-cv-01201: Answer to Complaint, Separate Defenses, and Counterclaims (Document 10), dated Sep. 15, 2017.
*Teva Pharmaceuticals International GMBH, et al. v. Fresenius Kabi USA, LLC.*—Civil Action No. 1:17-cv-01201: Answer to Fresenius Kabi USA, LLC's Counterclaims (Document 14), dated Oct. 6, 2017.
*Teva Pharmaceuticals International GMBH, et al. v. Mylan Laboratories Limited*—Civil Action No. 1:17-cv-01790: Complaint (Document 1), dated Dec. 12, 2017.
*Teva Pharmaceuticals International GMBH, et al. v. Mylan Laboratories Limited*—Civil Action No. 1:17-cv-01790: Defendant Mylan Laboratories Limited's Answer to Complaint for Patent Infringement (Document 12), dated Feb. 14, 2018.
*Teva Pharmaceuticals International GMBH, et al. v. Slayback Pharma Limited Liability Company*—Civil Action No. 1:18-cv-00117: Complaint (Document 1), dated Jan. 19, 2018.
*Teva Pharmaceuticals International GMBH, et al. v. Slayback Pharma Limited Liability Company*—Civil Action No. 1:18-cv-00117: Defendant Slayback Pharma Limited Liability Company's Answer to Complaint, Addtional Defenses and Counterclaims (Document 9), dated Feb. 12, 2018.
*Eagle Pharmaceuticals, Inc., et al. v. Hospira, Inc.*—Civil Action No. 1:18-cv-01074: Complaint (Document 1), dated Jul. 19, 2018.
*Eagle Pharmaceuticals, Inc., et al. v. Hospira, Inc.*—Civil Action No. 1:18-cv-01074: Defendant Hospira, Inc's Motion to Dismiss (Document 13), dated Aug. 31, 2018.
*Eagle Pharmaceuticals, Inc., et al. v. Hospira, Inc.*—Civil Action No. 1:18-cv-01074: Hospira, Inc's Brief in Support of its Rule 12(b)(6) Motion to Dismiss Plaintiffs' Complain (Document 20), public version dated Sep. 7, 2018.
*Eagle Pharmaceuticals, Inc., et al. v. Hospira, Inc.*—Civil Action No. 1:18-cv-01074: Exhibit Index—Includes Confidential Information (Document 21), public version dated Sep. 7, 2018.
*Eagle Pharmaceuticals, Inc., et al. v. Hospira, Inc.*—Civil Action No. 1:18-cv-01074: Plaintiffs' Opposition to Motion to Dismiss (Document 26), redacted—public version dated Nov. 2, 2018.
*Eagle Pharmaceuticals, Inc., et al. v. Hospira, Inc.*—Civil Action No. 1:18-cv-01074: Hospira's Reply Brief in Support of its Motion to Dismiss Plaintiffs' Complaint (Document 29), public version dated Nov. 26, 2018.
*Eagle Pharmaceuticals, Inc. v. Slayback Pharma LLC*—Civil Action No. 1:18-cv-01459: Complaint (Document 1), dated Sep. 20, 2018.
*Eagle Pharmaceuticals, Inc. v. Slayback Pharma LLC*—Civil Action No. 1:18-cv-01459: Defendant Slayback Pharma Limited Liability Company's Answer to Complaint, Additional Defenses, and Counterclaims (Document 9), dated Oct. 10, 2018.
*Eagle Pharmaceuticals, Inc. v. Slayback Pharma LLC*—Civil Action No. 1:18-cv-01459: Answer to Slayback Pharma LLC's Counterclaims (Document 13), dated Oct. 31, 2018.
*Teva Pharmaceuticals International GMBH, et al. v. Fresenius Kabi, LLC., et al.*—Civil Action No. 1:18-cv-01586: Complaint (Document 1), dated Oct. 15, 2018.
*Teva Pharmaceuticals International GMBH, et al. v. Fresenius Kabi, LLC., et al.*—Civil Action No. 1:18-cv-01586: Defendant Fresenius Kabi USA, LLC's Answer to Complaint, Separate Defenses, and Counterclaims (Document 9), dated Nov. 6, 2018.
*Teva Pharmaceuticals International GMBH, et al. v. Fresenius Kabi, LLC., et al.*—Civil Action No. 1:18-cv-01586: Defendant Mylan Laboratories LTD.'s Answer to Complaint for Patent Infringement (Document 11), dated Nov. 9, 2018.
*Teva Pharmaceuticals International GMBH, et al. v. Fresenius Kabi, LLC., et al.*—Civil Action No. 1:18-cv-01586: Answer to Fresenius Kabi USA, LLC's Counterclaims (Document 13), dated Nov. 27, 2018.
*Eagle Pharmaceuticals, Inc. v. Slayback Pharma LLC*—Civil Action No. 1:18-cv-01953: Complaint (Document 1), dated Dec. 11, 2018.
*Eagle Pharmaceuticals, Inc. v. Slayback Pharma LLC*—Civil Action No. 1:18-cv-01953: Defendant Slayback Pharma Limited Liability Company's Answer to Complaint, Additional Defenses, and Counterclaims(Document 11), public version dated Dec. 20, 2018.
*Eagle Pharmaceuticals, Inc. v. Slayback Pharma LLC*—Civil Action No. 1:18-cv-01953: Answer to Slayback Pharma LLC's Counterclaims (Document 12), dated Jan. 3, 2019.
*Eagle Pharmaceuticals, Inc. v. Slayback Pharma LLC*—Civil Action No. 1:18-cv-01953: Opening Brief in Support of Slayback Pharma Limited Liability Company's Motion for Judgment on the Pleadings (Document 17), public version dated Jan. 11, 2019.
*Eagle Pharmaceuticals, Inc. v. Slayback Pharma LLC*—Civil Action No. 1:18-cv-01953: Eagle Pharmaceuticals' Opposition to Slayback Pharma's Motion for Judgment on the Pleadings (Document 23), redacted—public version dated Feb. 12, 2019.

(56) References Cited

OTHER PUBLICATIONS

*Eagle Pharmaceuticals, Inc.* v. *Slayback Pharma LLC*—Civil Action No. 1:18-cv-01953: Reply Brief in Further Support of Slayback Pharma Limited Liability Company's Motion for Judgment on the Pleadings (Document 27), public verison dated Mar. 1, 2019.
Interlocutory decision in Opposition proceedings of EP 2528602 issued Apr. 8, 2019.
Remington's Pharmaceutical Sciences, 18th edition, (1990), p. 1322.
U.S. Pharmacopeia 32-NF-27—General Notices and Requirements (2009).
Renu Chadha, et al., "Drug Carrier Systems for Anticancer Agents: a Review", Journal of Scientific & Industrial Reasearch, vol. 67, pp. 185-197, 2008.
American Heart Association, "Living With Heart Failure" (https://www.heart.org/idc/groups/heart- public/@wcm/@hcm/@gwtg/documents/downloadable/ucm_309068.pdf) (2001).
American Society of Hospital Pharmacists. ASHP Technical Assistance Bulletin on Hospital Distribution and Control. Am J. Hosp. Pharm. 1980, 37:1097-103.
Baldi et al., Statistical Procedures for Optimizing the Freeze-Drying of a Model Drug in Tert-Butyl Alcohol: Water Mixtures, Eur. J. of Pharm. & Biopharm. 40(3):138-41 (1994).
Bergsagel et al., Effect of cyclophosphamide on Advanced Lung Cancer and the Hematological Toxicity of Large, Intermittent Intravenous Doses, Canad. Med. Ass. J., 98, 532-538 (1968).
Bernard Testa, et al., "Hydrolysis in Drug and Prodrug Metabolism", Verlag Helvetica Chimica Acta, pp. 681-684, 2003, ISBN 3-906390-25-X.
Biewenga et al., "The Pharmacology of the Antioxidant Lipoic Acid," Gen. Pharmac., vol. 39, No. 3, pp. 315-331 (1997).
Boylan et al., Parenteral Products, Chapter 12 in Banker, et al., Modern Pharmaceutics, Fourth Ed. (2002).
Brigitte C. Scott, et al., Lipoic and Dihydrolipoic Acids . . . , Free Rad. Res., vol. 20, No. 2, pp. 119-133, 1994.
Broadhead, Pharmaceutical Preformulation and Formulation, Chapter 9 in "Parenteral Dosage Forms," (Interpharm) 2001.
Canadian Society of Hospital Pharmacists: Guidelines for Drug-Use Control, 2008.
Center for Drug Evaluation and Research, Andrew Dmytrijuk, FDA Medical Review for the Approval of Bendeka (2015).
Charles P. Carpenter, et al., "A Study of the Polyethylene Glycols as Vehicles for Intramuscular and Subcutaneous Injections", Journal of the American Pharmaceutical Association, vol. XII, No. 1, pp. 27-29, 1952.
Cheson et al., Bendamustine: Rebirth of an Old Drug, J. Clin. Oncol. 27, 1492-1501 (2009).
Cheung et al., Safety and Pharmacokinetics of Bendamustine Rapid-Infusion Formulation, J. of Clinical Pharmacology 2017.00(0) 1-11.
Chu et al., Common Chemotherapy Regimens in Clinical Practice, Physicians' Cancer Chemotherapy Drug Manual 2009.
Derry E. Wilman, Application of 15N Nuclear Magnetic Resonance . . . , J. Med. Chem., vol. 38, pp. 2256-2258, 1995.
E. Santacesaria, et al., "Thermal Stability of Nonionic Polyoxyalkylene Surfactants", Journal of Applied Polymer Science, vol. 42, pp. 2053-2061, 1991.
EC Safety Data Sheet: Ribomustin® 2007.
Eric Watson, et al., Kinetics of Phosphoramide Mustard . . . , Journal of Pharmaceutical Sciences, vol. 74, No. 12, pp. 1283-1292, 1985.
Eugene C. Corbett, Jr., Intravenous Fluids: It's More Than Just 'Fill 'Er Up!', Series #52 Practical Gastroenterology 44-60 (2007).
Flamberg et al., Low Temperature Vacuum Drying of Sterile Parenterals From Ethanol, Bulletin of the Parenteral Drug Association, 24(5):209-17 (1970).
Floss et al., Intravenous fluids principles of treatment, Clinical Pharmacist, 3:274-283 (Oct. 2011).
Friedberg et al., Bendamustine in Patients with Rituximab-Refractory Indolent and Transformed Non-Hodgkin's Lymphoma: Results from a Phase II Multicenter, Single-Agent Study, J. Clin. Oncol., 26(2):204-210 (2008).
Fujisawa Deutschland GmbH Ribomustin® Products and Technical Specifications.
Galacid Excel 88 fact sheet (lactic acid 88%), www.lactic.com, 2012.
Gandhi & Burger, Bendamustine in B cell malignancies: the new, 46-year old kid on the block, Clin Cancer Res. Dec. 15, 2009; 15(24):7456-7461.
Glimelius et al., Bolus-Injection (2-4 min) Versus Short-term (10-20 min) Infusion of 5-Fluorouracil in Patients with Advanced Colorectal Cancer: a Prospective Randomised Trial, Eur J. Cancer, 34, 674-678 (1998).
Gust and Krauser, Investigations on the Stability of Bendamustin, a Cytostatic Agent of the Nitrogen Mustard Type I. Synthesis, Isolation, and Characterization of Reference Substances, in Monatshefte für Chemie, 128:291-99 (1997).
Heider et al., Efficacy and Toxicity of Bendamustine in Patients with Relapsed Low-Grade non-Hodgkin's Lymphomas, Anticancer Drugs, 12, 725-729 (2001).
HFSA Guidelines, Journal of Cardiac Failure vol. 16 No. 6 (2010).
ICH Harmonised Tripartite Guideline, Stability testing of New Drug Substances and Products Q1A(R2), dated Feb. 6, 2003.
International Conference on Harmonisation in Guideline on Impurities in New Drug Products: Availability, 62 Fed. Reg. 27,454-27,461 (May 19, 1997).
International Search Report and Written Opinion for No. PCT/US2013/032289 dated Jun. 6, 2013. (5 Pages).
International Search Report and Written Opinion issued in counterpart PCT/US2013/032295 dated Jun. 3, 2013 (4 pages).
International Search Report and Written Opinion issued in counterpart PCT/US2013/26187 dated May 6, 2013 (2 pages).
International Search Report and Written Opinion of International application based on PCT/US2011/022958, dated Apr. 12, 2011 (8 pages).
Jay S. Trivedi, et al., Water-Insoluble Drug Formulation, 7. Solubilization Using CoSolvent Approach, pp. 141-168, 2000.
Jay S. Trivedi, Water-Insoluble Drug Formulation, Second Edition, 9 Solubilization Using Cosolvent Approach, pp. 161-194, 2008.
JC Price, Handbook of Pharm. Excipients, 5th Edition, Polyethylene Glycol, pp. 545-550, Aug. 9, 2005.
Jerry March, Advanced Organic Chemistry (4th ed., John Wiley & Sons, Inc. 1992).
John D. Roberts & Marjorie C. Caserio, Basic Principles of Organic Chemistry 612-13, 615-16, 617-18 (W. A. Benjamin, Inc., 2d ed. 1977).
Jonkman-de Vries et al., Pharmaceutical Development of (Investigational) Anticancer Agents for Parental Use—A Review, Drug Dev Ind Pharm. 22(6):475-494 (1996).
Julia A. Barman Balfour, et al., "Bendamustine", Drugs, vol. 61, No. 5, pp. 631-638, 2001.
Kalaycio. M., Clinical Experience With Bendamustine: A New Treatment for Patients With Chronic Lvmphocytic Leukemia; Clin Leukemia. 2008; 2(4): 223-229.
Kenneth E. Avis, et al., Remington, Parenteral Preparations, Chapter 41, pp. 780-786, 2000.
Knauf et al., Bendamustine Versus Chlorambucil in Treatment-Naive Patients with B-Cell Chronic Lymphocytic Leukemia (B-CLL): Results of an International Phase III Study, Blood, 110 (11), 609a (abstract 2043) (2007).
Koomans et al., Sodium Balance in Renal Failure: A Comparison of Patients with Normal Subjects Under Extremes of Sodium Intake, Hypertension 7:714-721 (1985).
Kurt H. Bauer, et al., Pharmazeutische Technologies, pp. 225-228, HW9, 1993.
Kurt H. Bauer, et al., Pharmazeutische Technologies, pp. 424-425, HW10, 1993.
Larry A. Gatlin, et al., Injectable Drug Development, 17. Formulation and Administration . . . Products, pp. 401-420, Informa Healthcare, 2008, ISBN 13: 978-1-5749-1095-7.
Gibson et al., "Pharmaceutical preformulation and formulation: A practical guide from candidate drug selection to commercial dosage form", Informa Healthcare USA, 2009, vol. 199, 2d ed, pp. 1-559.

(56) References Cited

OTHER PUBLICATIONS

"Draft Note for Guidance on Excipients, Antioxidants and Antimicrobial Preservatives in the Dossier for Application for Marketing Authorisation of Medicinal Product", EMEA, 2003, pp. 1-10.
Leonard & Jann, A New Synthesis of Aziridinium Salts. 2,2-Pentamethylene-1,1-tetramethyleneaziridinium Perchlorate, A Prototype, 82 J. Am. Chemistry Soc'y 6418-6419 (1960).
Leoni et al., SDX-105 (Bendamustine), a Clinically Active Antineoplastic Agent Possesses a Unique Mechanism of Action, Abstract, 102(11) Blood, Abstract #2363 (Nov. 16, 2003).
Lian-Feng Huang, et al., Water-Insoluble Drug Formulation, Second Edition, Ch. 7. Formulation Strategies and Practice . . . Support, pp. 113-132, 2008, ISBN 13: 978-0-8493-9644-1.
Lissitchkov et al., Phase-I/II study to Evaluate Dose Limiting Toxicity, Maximum Tolerated Dose, and Tolerability of Bendamustine HCl in Pre-treated Patients With B-Chronic Lymphocytic Leukaemia (Binet stages B and C) Requiring Therapy, J. Cancer Res. Clin. Oncol. 132:99-104 (2006).
Liu (ed). Water-Insoluble Drug Formulation, 1st ed., CRC Press, Chapters 7 and 9, 2000.
Liu (ed). Water-Insoluble Drug Formulation, 2nd ed., CRC Press, Chapters 7 and 9, 2000.
Lyondell Tebol® 99, Tertiary Butyl Alcohol in Freeze-Drying Applications,(Lyondell Chemical Co., 2003).
Lyophilization of Biopharmaceuticals (Henry R. Costantino & Michael K. Pikal eds., Association of Pharmaceutical Scientists 2004).
Maas et al., "Stabilitat von Bendamustinhydrochlorid in Infusionslosungen," Die Pharmazie, Govi Verlag Pharmazeutischer Verlag GMBH, vol. 49, No. 10 pp. 775-777 (1994). (Abstract Only).
Margolin et al., Shortening the Infusion Time of Anticancer Drugs: Who Will Benefit?, J. of Clinical Oncology, 25(19):2642-2643 (2007).
McGinity, et al., Journal of Pharmaceutical Sciences, Influence of Peroxide Impurities in Polyethylene Glycols . . . , vol. 64, No. 2 pp. 356-357, 1975.
Michael J. Akers, "Excipient-Drug Interactions in Parentaral Formulations," Journal of Pharmaceutical Sciences, vol. 91, Issue 11, pp. 2283-2300, 2002.
Michael J. Akers, Remington, The Science and Practice of Pharmacy 21st Edition,Parenteral preparation, chapter 41, pp. 802-835, 2005.
Michael P. Gamcsik, et al., NMR Studies of the Conjugation . . . , J. Med. Chem., vol. 33, pp. 1009-1014, 1990.
National Kidney Foundation, "Clinical Practice Guidelines and Clinical Practice Recommendations" (http://kidneyfoundation.cachefly.net/professionals/KDOQI/guideline_upHD_PD _VA/hd_guide5.htm) (2006).
Neelam Seedher, et al., Solubilization of Nimesulide; Use of Co-solvents, Indian J. Pharm. Sci., vol. 65, No. 1, pp. 58-61, 2003.
Nema et al., Excipients and Their Use in Injectable Products, PDA J. Pharma. Sci. & Tech., 51(4):166-171 (Jul.-Aug. 1997).
Ni et al., Stabilization and Preformulation of Anticancer Drug—SarCNU, Int'l J. of Pharma., 249:257-264 (2002).
Ni et al., Use of Pure t-Butanol as a Solvent for Freeze-Drying: A Case Study, Int'l. J. of Pharma., 226:39-46 (2001).
Nuijen et al., Pharmaceutical Development of a Parenteral Lyophilized Formulation of the Novel Antitumor Agent Aplidine, PDA J. Pharmaceut. Sci. and Technol. 54(3):193-208 (May-Jun. 2000).
O'Connor, Hydrolysis and Alkylating Reactivity of Aromatic Nitrogen Mustards, J.Chem. Soc. Perkin Trans. 2, 1933-1939 (1991).
Orrie M. Friedman, et al., "Colorimetric Estimation of Nitrogen Mustards in Aqueous Media", Analytical Chemistry, vol. 33, No. 7, pp. 906-910, 1961.

Ozegowski et al., IMET 3393, ?-[1-Methyl-5-bis-(β-chloroethyl)-amino-benzimidazolyl-(2)]-butyric acid hydrochloride, a new cytostatic agent from the benzimidazole mustard gas series, 110 Zbl Pharm. 1013-1019 (1971).
Paul J. Sheskey, Handbook of Pharmaceutical Excipients, 7th Edition, Propyl Gallate, 2012.
Poulsen, Introduction to Chemistry (2010).
Pramod K. Gupta, et al., "Injectable Drug Development Techniques to Reduce Pain and Irritation", pp. 183, Informa Healthcare, 2008, ISBN 13: 978-1-5749-1095-7.
Preiss et al., "Pharmacological and clinical date of Bendamustine," 17th International Cancer Congress, pp. 1637-1640 (1998).
Preiss et al., Studies on the Pharmacokinetics of Bendamustine (Cytostasan®) in Humans, Pharmazie, 40(11):782-784 (1985).
R.A. Pethrick et al., Excerpt from Polymer Yearbook 13, CRC Press, Oct. 1, 1996, Technology & Engineering Vinogradova et al.
Rassachaert et al., "A phase 1 study of bendamustine hydrochloride administered once every 3 weeks in patients with solid tumors," Anti-Cancer Drugs, vol. 18 No. 5 pp. 587-595 (2007).
Remington's Pharmaceutical Sciences, 18th edition, (1990), pp. 1286-1288.
Remington's Pharmaceutical Sciences 1990 (Eighteenth Edition), Mack Publishing Company, Chapter 85, 1570-1580.
Ribomustin Monograph (Updated Aug. 2005).
Ribomustin Monograph (Updated Jan. 2002).
Ribomustin Product Information, Janssen-Cilag Pty Ltd (Updated Sep. 15, 2016).
Rote Liste 1996 for Ribomustin (86 023).
Rote Liste 2003 for Ribomustin (86 045).
Rowe et al., "Handbook of Pharmaceutical Excipients," Pharmaceutical Press, 6th edition pp. 857 (extract from index) (2009).
Rowe et al., "Handbook of Pharmaceutical Excipients," Pharmaceutical Press, 6th edition, pp. 454-455 (2009).
Raymond C. Rowe and Paul J. Sheskey, et al., Handbook of Pharmaceutical Excipients, 7th Edition, Pharmaceutical Press, Propyl Gallate, pp. 668-669.
Rowe, et al., "Handbook of Pharmaceutical Excipients," Pharmaceutical Press, 5th edition, pp. 545-550, Polyethylene Glycol, (2006).
Safety Data Sheet, Lactic Acid, 88%, Columbus Chemical Industries, 2013.
Scasnar at al., Radiochemical Assay of Stability of 14C-Cytostasan Solutions During Preparation and Storage, Journal of Radioanalytical and Nuclear Chemistry, Articles 121(2):489-497 (1988).
Schoffski et al., "Weekly administration of bendamustine: A phase 1 study in patients with advanced progressive solid tumors," Annals of Oncology II, pp. 729-734 (2000).
Schoffski et al., Repeated administration of short infusions of bendamustine: a phase 1 study in patients with advanced progressive solid tumors, J. Cancer Res Clin Oncol, vol. 126 No. 1 pp. 41-47 (2000).
Schwänen et al., In vitro evaluation of bendamustine induced apoptosis in B-chronic lymphocytic leukemia, Leukemia 16:2096-2105 (2002).
SciFinder, Hydrolytic degradation of IMET 3393, American Chemical Society, 2018.
Seager et al., Structure of Products Prepared by Freeze-Drying Solutions Containing Organic Solvents, PDA Journal of Pharmaceutical Science and Technology, 39(4):161-179 (1985).
Search History issued in connection with PCT/US2013/32295 dated May 10, 2013.
Shah et al., Physical, Chemical, and Bioavailability Studies of Parenteral Diazepam Formulations Containing Propylene Glycol and Polyethylene Glycol 400, Drug Development and Industrial Pharm.), 17:12, 1635-1654 (Oct. 20, 2008).

\* cited by examiner

FORMULATIONS OF BENDAMUSTINE

CROSS-REFERENCE TO RELATED APPLICATIONS

This application is a continuation of application Ser. No. 16/015,656, filed Jun. 22, 2018, which is a continuation of application Ser. No. 15/432,335, filed Feb. 14, 2017, now U.S. Pat. No. 10,010,533, issued Jul. 3, 2018, which is a continuation of application Ser. No. 15/013,436, filed Feb. 2, 2016, now U.S. Pat. No. 9,572,797, issued Feb. 21, 2017, which is a continuation of application Ser. No. 14/031,879, filed Sep. 19, 2013, now U.S. Pat. No. 9,265,831, issued Feb. 23, 2016, which is a continuation of application Ser. No. 13/016,473, filed Jan. 28, 2011, now U.S. Pat. No. 8,609,707, issued Dec. 17, 2013, which claims the benefit of U.S. Provisional Patent Application No. 61/299,100, filed Jan. 28, 2010, the contents of each of which are incorporated herein by reference.

BACKGROUND OF THE INVENTION

Bendamustine free base is represented by the following structural formula (I)

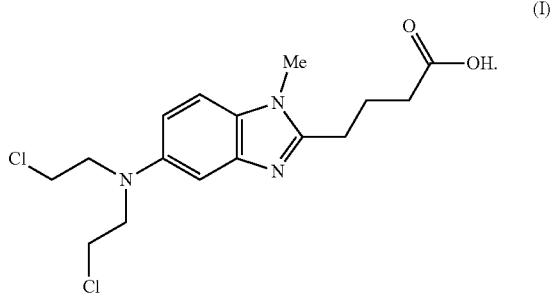 [SMILES: Cn1c(CCCC(=O)O)nc2cc(N(CCCl)CCCl)ccc21]

Bendamustine is used in the treatment of a number of cancers including leukemias, Hodgkins disease and multiple myelomas. Bendamustine is the active ingredient of the commercial product Treanda™, a lyophilized powder for reconstitution.

Bendamustine exhibits rapid degradation upon reconstitution of the lyophilized product. Bendamustine undergoes hydrolysis by direct substitution rather than an addition elimination process due to the presence of the highly labile aliphatic chlorine atoms. Some of the main degradants of bendamustine are the monohydroxy compound known as HP1 (hydrolysis product 1) and dihydroxy compound HP2 (hydrolysis product 2). The monohydroxy compound appears as the main impurity at Relative Retention Time (RRT) 0.6 and the dihydroxy compound appears as the main impurity at RRT 0.27. Minor peaks appear at RRT 1.2, which are presently unknown.

The stability of bendamustine in water is measured in hours, and is therefore, not suitable for long-term storage in liquid form. The lyophile possesses good chemical stability. However, reconstitution of the lyophile is clinically inconvenient, taking 15-30 mins with implications of chemical instability. There is a need for ready to use (RTU) bendamustine formulations having enhanced stability.

SUMMARY OF THE INVENTION

In other aspects of the invention, the bendamustine-containing compositions include a) a pharmaceutically acceptable fluid which contains one or more of propylene glycol, ethanol, polyethylene glycol, benzyl alcohol and glycofurol, and b) a stabilizing amount of a chloride salt. In other aspects of the invention, the bendamustine-containing compositions include DMSO (dimethyl sulfoxide) as part of the pharmaceutically acceptable fluid included therein. Regardless of the pharmaceutically acceptable fluid included, the amount of bendamustine included in the composition is preferably from about 20 mg/mL to about 60 mg/mL. Still further aspects of the invention include methods of treatment using bendamustine-containing compositions and kits containing the same.

One of the advantages of the inventive liquid compositions is that they have substantially improved long term stability when compared to currently available formulations. For example, the inventive bendamustine compositions are substantially free of impurities after at least about 15 months at a temperature of from about 5° C. to about 25° C. The inventive formulations are advantageously ready to use or ready for further dilution. Reconstitution of lyophilized powders is not required.

DETAILED DESCRIPTION OF THE INVENTION

Unless defined otherwise, all technical and scientific terms used herein have the same meaning as is commonly understood by one of ordinary skill in the art to which this invention belongs. In the event that there is a plurality of definitions for a term herein, those in this section prevail unless stated otherwise.

As used herein, RRT is calculated by dividing the retention time of the peak of interest by the retention time of the main peak. Any peak with an RRT<1 elutes before the main peak, and any peak with an RRT>1 elutes after the main peak.

For purposes of the present invention, "substantially free of impurities" shall be understood to include bendamustine-containing compositions in which the amount of total impurities is less than about 5%, as calculated on a normalized peak area response ("PAR") basis as determined by high performance liquid chromatography ("HPLC") at a wavelength of 223 nm, after a period of about 15 months at a temperature of from about 5° C. to about 25° C. The amount of impurities is further calculated as being based upon the original amount bendamustine (or salt thereof) being present in the composition or formulation.

For purposes of the present invention, a pharmaceutically acceptable fluid is a fluid which is suitable for pharmaceutical use.

Preferably, the amount of any individual degradant in the inventive compositions does not exceed 2% PAR as determined by HPLC at a wavelength of 223 nm after storage periods of at least about 15 months at a temperature of from about 5° C. to about 25° C. In some aspects, the amount of time the inventive compositions demonstrate long term storage stability is at least about 18 months and preferably at least about 2 years when stored under the conditions described herein.

In accordance with one aspect of the invention there are provided long term storage stable bendamustine-containing compositions including:
  a) bendamustine or a pharmaceutically acceptable salt thereof; and
  b) a pharmaceutically acceptable fluid including
    i) PEG, PG or mixtures thereof; and
    ii) a stabilizing amount of an antioxidant.

The total impurities in the inventive compositions resulting from the degradation of the bendamustine in the compositions is less than about 5% PAR as determined by HPLC at a wavelength of 223 nm after at least about 15 months at a temperature of from about 5° C. to about 25° C., and thus have long term stability for at least the same period of time or longer. Preferably, the bendamustine-containing compositions demonstrate long term storage stability for at least about 2 years, especially when stored at the lower (refrigerated) temperatures. In one embodiment, the amount of total impurities in the inventive compositions resulting from the degradation of the bendamustine is less than about 3% PAR as determined by HPLC at a wavelength of 223 nm after at least about 2 years at a temperature of from about 5° C. to about 25° C.

In some aspects of the invention, the bendamustine concentration in the inventive compositions is from about 10 mg/mL to about 100 mg/mL, preferably 20 mg/mL to about 60 mg/mL. Preferably the bendamustine concentration in the inventive compositions is from about 25 mg/mL to about 50 mg/mL, and more preferably from about 30 mg/mL to about 50 mg/mL. It will be understood that compositions containing any useful concentration within the ranges, i.e. 10, 20, 25, 30, 35, 40, 45, 50, 55, 60 . . . 100 are contemplated. In other embodiments, the bendamustine concentration in the composition is about 50 mg/mL. In alternative aspects, the amount of bendamustine is outside these ranges but the amounts will be sufficient for single or multiple administrations of dosages generally regarded as effective amounts.

In several embodiments of the invention, pharmaceutically acceptable fluid is non-aqueous and may be, but is not necessarily, a solvent for the bendamustine or salt thereof. Within this aspect, the pharmaceutically acceptable fluid is propylene glycol (PG) or polyethylene glycol (PEG). In other embodiments of the invention however, the pharmaceutically acceptable fluid is a mixture of PEG and PG. For example, the pharmaceutically acceptable fluid can include about 50% PEG and about 50% PG. Alternatively, pharmaceutically acceptable fluid includes about 95% PEG and about 5% PG. The amount of PEG and PG can also be varied within the ranges, i.e. the ratio of PEG:PG in the pharmaceutically acceptable fluid can range from about 95:5 to about 50:50. Within this range, is a pharmaceutically acceptable fluid containing about 75% PEG and about 25% PG, and preferably 80% PEG and 20% PG. In another embodiment, a pharmaceutically acceptable fluid can include about 85% PEG and about 15% PG while another preferred pharmaceutically acceptable fluid includes about 90% PEG and about 10% PG. The molecular weight of the PEG will be within the range of pharmaceutically acceptable weights although PEG 400 is preferred in many aspects of the invention.

Without meaning to be bound by any theory or hypothesis, the hydroxide of the polyethylene glycol molecule is less reactive than the hydroxides of propylene glycol. As a result, the ester forms at a slower rate in polyethylene glycol than propylene glycol and the resulting bendamustine degradants are unexpectedly and substantially reduced over extended periods of time when PEG is a substantial part of the pharmaceutically acceptable fluid.

The bendamustine-containing compositions according to several preferred aspects of the invention include a stabilizing amount of an antioxidant. For purposes of the present invention, "stabilizing amount" shall be understood to include those amounts which increase or enhance the stability of the bendamustine in the compositions described herein. The presence of one or more antioxidants described herein thus contributes, at least in part to the long term stability of the composition. Within this guideline, suitable antioxidant concentrations in the compositions can range from about 2.5 mg/mL to about 35 mg/mL, and preferably from about 5 mg/mL to about 20 mg/mL or from about 10 mg/mL to about 15 mg/mL. In some other embodiments, the concentration of the antioxidant in the bendamustine-containing composition is about 5 mg/mL.

Suitable antioxidants for inclusion include those which are pharmaceutically acceptable for use in human and veterinary formulations although not limited to those currently regarded as safe by any regulatory authority. For example, the antioxidant can be selected from among lipoic acid, thioglycerol (also known as monothioglycerol) and analogs thereof, propyl gallate, methionine, cysteine, metabisulfites, sodium formaldehyde sulfoxylate, phenol-containing aromatic and aliphatic compounds, dihydrolipoic acid and mixtures of the foregoing. Preferably, the antioxidant is thioglycerol, lipoic acid or a mixture thereof. Some particularly preferred embodiments of the invention include thioglycerol.

In view of the foregoing, some preferred long term storage stable bendamustine-containing compositions in accordance with the invention compositions include:
I. a) bendamustine or a pharmaceutically acceptable salt thereof; and
   b) a pharmaceutically acceptable fluid including
     i) polyethylene glycol and propylene glycol; and
     ii) a stabilizing amount of thioglycerol; or
II. a) about 50 mg/mL bendamustine or a pharmaceutically acceptable salt thereof; and
   b) a pharmaceutically acceptable fluid including
     i) about 90% PEG and about 10% PG; and
     ii) about 2.5 mg/mL thioglycerol.

Each of these compositions have the same stability profiles already described, i.e. having less than about 5% total impurities, PAR as determined by HPLC at a wavelength of 223 nm, after at least about 15 months of storage at a temperature of from about 5° C. to about 25° C.

In accordance with other aspects of the invention, there are provided long term storage stable bendamustine-containing compositions, including:
a) bendamustine or a pharmaceutically acceptable salt thereof;
b) a pharmaceutically acceptable fluid including one or more of the following: PG, ethanol, PEG, benzyl alcohol and glycofurol; and
c) a stabilizing amount of a chloride salt.

These compositions also have the low levels of impurities and long term stability mentioned herein. Preferred pharmaceutically acceptable fluids include PG, PEG or ethanol in this embodiment of the invention. Preferably, the PEG is PEG 400. If desired, glycerin and/or 88% (w/w) lactic acid can be added to the pharmaceutically acceptable fluid.

Suitable chloride salts include but are not limited to organic chloride salts, sodium chloride, choline chloride, hydrochloride salts of amino acids and mixtures thereof. Thus, as will be appreciated by those of ordinary skill, one can select from among a number of suitable chloride salts and it is Applicants' intention that the scope of the invention includes all such chloride salts that are capable of being included in bendamustine-containing formulations for extended periods without having a deleterious effect on the drug. In one embodiment of the invention, the chloride salt concentration is from about 10 to about 300 mg/mL. In another embodiment, the chloride salt concentration is from about 50 to about 215 mg/mL. In one preferred embodiment, the chloride salt concentration is about 215 mg/mL.

In accordance with another aspect of the invention, there is provided long term storage stable bendamustine-containing compositions, including:
   a) bendamustine or a pharmaceutically acceptable salt thereof; and
   b) a pharmaceutically acceptable fluid including DMSO.

These compositions also have the low levels of impurities and long term stability mentioned herein. In some aspects, the bendamustine concentration in these compositions is from about 10 mg/mL to about 100 mg/mL. Preferably, the bendamustine concentration is from about 20 mg/mL to about 50 mg/mL, more preferably from about 25 mg/mL to about 50 mg/mL. In an alternative embodiment, the bendamustine concentration is about 50 mg/mL.

Another embodiment of the invention provides methods of treating cancer in mammals. The methods include administering to a mammal in need thereof an effective amount of one of the bendamustine-containing compositions described herein. Since the active ingredient portion of the inventive composition is an FDA-approved drug, those of ordinary skill will recognize that the doses of bendamustine employed in this aspect of the invention will be similar to those employed in any treatment regimens designed for bendamustine as marketed under the trade name TREANDA. The patient package insert containing dosing information is incorporated herein by reference. The methods of treatment also include administering the inventive formulations for any purpose or physical condition for which bendamustine has been indicated as being useful.

Another embodiment of the invention includes methods of preparing bendamustine-containing compositions described herein. The methods include reconstituting lyophilized bendamustine in a pharmaceutically acceptable fluid containing one of the following:
   A) i) PEG, PG or mixtures thereof; and
      ii) a stabilizing amount of an antioxidant;
   B) i) one or more of PG, ethanol, PEG, benzyl alcohol and glycofurol; and
      ii) a stabilizing amount of a chloride salt; or
   C) DMSO.

The steps are carried out under pharmaceutically acceptable conditions for sterility and manufacturing.

In a further aspect of the invention, there are provided methods of controlling or preventing the formation of impurities in bendamustine-containing compositions during long term storage. The methods include combining an amount of bendamustine or a pharmaceutically acceptable salt thereof with a sufficient amount of a pharmaceutically acceptable fluid containing one of the following:
   A) i) PEG, PG or mixtures thereof; and
      ii) a stabilizing amount of an antioxidant;
   B) i) one or more of PG, ethanol, PEG, glycofurol and benzyl alcohol; and
      ii) a stabilizing amount of a chloride salt; or
   C) DMSO.

Further optional steps in accordance therewith include transferring one or more pharmaceutically acceptable doses of the formulations into a suitable sealable container and storing the sealed container at a temperature of from about 5° C. to about 25° C. As a result of carrying out these steps, it is possible to control or substantially prevent the formation of impurities which otherwise occur with bendamustine-containing compositions during long term storage so that the artisan is provided with bendamustine-containing formulations having less than about 5% total impurities PAR as determined by HPLC at a wavelength of 223 nm, after at least about 15 months of storage at a temperature of from about 5° C. to about 25° C.

The compositions of the present invention can be packaged in any suitable sterile vial or container fit for the sterile storage of a pharmaceutical such as bendamustine. Suitable containers can be glass vials, polypropylene or polyethylene vials or other special purpose containers and be of a size sufficient to hold one or more doses of bendamustine.

A further aspect of the invention includes kits containing lyophilized bendamustine or a pharmaceutically acceptable salt thereof in a first container or vial; and, in a second container, a sufficient amount of a pharmaceutically acceptable fluid such as those described herein, i.e. one of the following:
   A) i) PEG, PG or mixtures thereof; and
      ii) a stabilizing amount of an antioxidant;
   B) i) one or more of PG, ethanol, PEG, glycofurol and benzyl alcohol; and
      ii) a stabilizing amount of a chloride salt; or
   C) DMSO.

For purposes of this embodiment, the amount of fluid which is sufficient is an amount which allows the bendamustine to be dissolved or dispersed to a degree which renders the liquid composition ready for use.

As will be appreciated by those of ordinary skill, the kit will contain other pharmaceutically necessary materials for storing and/or administering the drug, including instructions for storage and use, additional diluents, if desired, etc.

EXAMPLES

The following examples serve to provide further appreciation of the invention but are not meant in any way to restrict the effective scope of the invention.

Example 1

Bendamustine-containing compositions were prepared by dissolving bendamustine HCl to a concentration of 10 mg/ml in one of ethanol, propylene glycol and benzyl alcohol as indicated in Table 1 below. 215 mg/ml of choline chloride was added in half of the samples as a source of soluble chloride ions. The samples were maintained at 40° C. and analyzed periodically for drug content and total impurities. The results obtained are presented in Table 1.

TABLE 1

Stability of Bendamustine HCl

| Formulation | Temp | Time | BDM mg/ml | % Total Impurities |
|---|---|---|---|---|
| BDM—10 mg/mL | Initial | | 10.43 | 0.27 |
| Choline chloride— | 40° C. | 48 hrs | 10.48 | 1.27 |
| 215 mg/mL | | 7 day | 10.26 | 2.11 |
| Ethanol qs to 1 mL | | | | |
| BDM—10 mg/mL | Initial | | 10.55 | 0.27 |
| Ethanol qs to 1 mL | 40° C. | 48 hrs | 10.30 | 2.39 |
| | | 7 day | 9.55 | 6.66 |
| BDM—10 mg/mL | Initial | | 9.99 | 0.21 |
| Choline chloride— | 40° C. | 48 hrs | 9.95 | 0.60 |
| 215 mg/mL | | 7 day | 9.43 | 2.31 |
| Propylene glycol qs to 1 mL | | | | |
| BDM—10 mg/mL | Initial | | 9.68 | 0.21 |
| Propylene glycol qs | 40° C. | 48 hrs | 9.45 | 0.88 |
| to 1 mL | | 7 day | 9.00 | 3.44 |
| BDM—10 mg/mL | Initial | | 9.95 | 1.19 |

TABLE 1-continued

Stability of Bendamustine HCl

| Formulation | Temp | Time | BDM mg/ml | % Total Impurities |
|---|---|---|---|---|
| Choline Chloride— 215 mg/mL Benzyl alcohol qs to 1 mL | 40° C. | 48 hrs 7 day | 9.89 8.97 | 3.51 4.24 |
| BDM—10 mg/mL Benzyl alcohol qs to 1 mL | 40° C. | Initial 48 hrs 7 day | 9.52 8.67 7.49 | 0.33 4.18 7.84 |

Note:
In Table 1 the total % impurities include total contributions from peaks at various RRTs.

As shown in Table 1, the bendamustine formulations are very stable in solutions containing solvent and chloride salt. Table 1 shows that bendamustine, when dissolved at a concentration of about 10 mg/mL, in a pharmaceutically acceptable fluid, such as ethanol and propylene glycol, and containing a stabilizing amount of a chloride salt, such as choline chloride, had less than about 5% after at least 7 days storage at 40° C.

The data presented in Table 1 translates to bendamustine-containing compositions including a pharmaceutically acceptable fluid and a stabilizing amount of a chloride salt having a shelf life of at least about 15 months at 5° C. and 25° C.

The sample including ethanol alone exhibited more than 6.5 total degradants after 7 days storage at 40° C. The sample including benzyl alcohol alone exhibited more than 7.5% total degradants after 7 days storage at 40° C. Bendamustine-containing compositions with such high levels of degradation would not be suitable for long-term storage.

Example 2

Bendamustine-containing compositions were prepared by dissolving bendamustine HCl to a concentration of 10 mg/ml in DMSO. The samples were maintained at 40° C. and analyzed periodically for drug content and impurity profile. The results obtained are presented in Table 2.

TABLE 2

Stability of Bendamustine HCl in DMSO

| Formulation | Temp | Time | Content (mg/mL) | % Total Imp |
|---|---|---|---|---|
| BDM—10 mg/mL DMSO qs to 1 mL | 40° C. | Initial 48 hrs 1 week | 10.2 9.80 10.0 | 0.23 0.30 0.56 |

Note:
In Table 2 the total % impurities include total contributions from peaks at various RRTs.

Table 2 shows that bendamustine, when dissolved in DMSO, had substantially no increase in total degradants. The data presented in Table 2 translates to bendamustine-containing compositions including DMSO having a shelf life of at least about 15 months at 5° C. and 25° C. In fact, such compositions are expected to have long term stability for periods beyond 15 months, i.e. up to 2 years or greater.

Example 3

Bendamustine-containing compositions were prepared by dissolving bendamustine HCl to a concentration of 20 mg/ml in polyethylene glycol 400 and 5 mg/ml of lipoic acid was added as a stabilizing antioxidant as indicated in Table 3 below. The samples were maintained at 40° C. or 25° C. and analyzed after 15 days for drug content and impurities. The results obtained are presented in Table 3.

TABLE 3

Stability of Bendamustine (20 mg/ml) in PEG 400 and Antioxidants

| Antioxidant | T ° C. | Time days | % Initial | % Imp RRT 0.58 | % Total Imps |
|---|---|---|---|---|---|
| None | 25 | 15 | 97.6 | 2.08 | 2.28 |
| | 40 | 15 | 56.3 | 2.17 | 41.9 |
| Lipoic Acid 5 mg/ml | 25 | 15 | 98.5 | <LD | 0.23 |
| | 40 | 15 | 97.5 | 0.33 | 0.53 |

<LD = Below Level of Detection

As shown in Table 3, bendamustine, when dissolved in a pharmaceutically acceptable fluid, such as polyethylene glycol, in the presence of a stabilizing amount of an antioxidant, such as lipoic acid, had substantially no increase in total degradants after a period of 15 days. The data presented in Table 3 translates to bendamustine-containing compositions including a pharmaceutically acceptable fluid and a stabilizing amount of an antioxidant having a shelf life of at least about 15 months at 5° C. and 25° C.

The sample including PEG alone, on the other hand, which did not contain an antioxidant, did not exhibit stabilizing effects at 40° C. This sample had more than 40% more total impurities than the sample including lipoic acid. Bendamustine-containing compositions with such high levels of total impurities would not be suitable for long-term storage.

Example 4

Bendamustine-containing compositions were prepared by dissolving bendamustine HCl to a concentration of 50 mg/ml in 90% polyethylene glycol 400 and 10% propylene glycol. 5 mg/ml of thioglycerol, α-lipoic acid or dihydrolipoic acid was added as a stabilizing antioxidant as indicated in Table 4 below. The samples were maintained at 40° C. and analyzed after 15 days or one month for drug content and impurity profile as indicated in Table 4 below. The results obtained are presented in Table 4.

TABLE 4

Stability of Bendamustine (50 mg/ml) in 90% PEG 400, 10% Propylene Glycol and Antioxidant

| Antioxidant | T (° C.) | Time | Content (mg/mL) | % Initial | % Impurities RRT | | % Total Imps |
|---|---|---|---|---|---|---|---|
| | | | | | HP1 0.59 | PG ester 1.10 | |
| Thioglycerol | 40 | initial | 48.8 | 100 | <LD | <LD | 0 |
| | 40 | 1 month | 48.5 | 99.4 | 0.06 | 0.20 | 0.71 |

TABLE 4-continued

Stability of Bendamustine (50 mg/ml) in 90%
PEG 400, 10% Propylene Glycol and Antioxidant

| Antioxidant | T (° C.) | Time | Content (mg/mL) | % Initial | % Impurities RRT HP1 0.59 | PG ester 1.10 | % Total Imps |
|---|---|---|---|---|---|---|---|
| α-lipoic acid | 40 | initial | 49 | 100 | <LD | <LD | 0 |
|  | 40 | 15 days | 48.8 | 99.6 | 0.19 | 0.13 | 0.32 |
|  | 40 | 1 month | 48.7 | 99.4 | 0.34 | 0.26 | 0.79 |
| Dihydrolipoic acid | 40 | initial | 49.3 | 100 | <LD | <LD | 0 |
|  | 40 | 1 month | 47.7 | 97.4 | 0.63 | 0.12 | 1.84 |

<LD = Below Level of Detection

As shown in Table 4, bendamustine, when dissolved in a pharmaceutically acceptable fluid, such as a combination of polyethylene glycol and propylene glycol, in the presence of a stabilizing amount of an antioxidant, such as thioglycerol, α-lipoic acid or dihydrolipoic acid, had substantially no increase in total degradants after a period of 1 month. This data supports the position that bendamustine-containing compositions according to the invention have a shelf life of at least about 2 years when stored at temperatures between 5° C. and 25° C.

Example 5

Bendamustine-containing compositions were prepared by dissolving bendamustine HCl to a concentration of 50 mg/ml in a mixture of polyethylene glycol 400 and propylene glycol as indicated in Table 5 below. 5 mg/ml of lipoic acid was added as a stabilizing antioxidant. The samples were maintained at 40° C., 25° C. and 5° C. and analyzed after 1 week, 15 days or one month for drug content and impurity profile as indicated in Table 5 below. The results obtained are presented in Table 5.

TABLE 5

Stability of Bendamustine (50 mg/ml) and Lipoic
Acid (5 mg/ml) in PEG400 and Propylene glycol

| Formulation | Temp. | Time Period | Content (mg/mL) | % of Initial | HP1 0.58 | PG ester 1.10 | PG ester 1.13 | % Total Imp. |
|---|---|---|---|---|---|---|---|---|
| BDM - 50 mg/mL Lipoic acid - 5 mg/mL PEG 400:PG (75:25) qs to 1 mL | | Initial | 49.6 | 100 | BDL | BDL | BDL | 0.18 |
| | 40° C. | 1 W | 49.0 | 98.8 | 0.05 | 0.13 | BDL | 0.38 |
| | | 15 d | 48.3 | 97.4 | 0.08 | 0.26 | BDL | 0.55 |
| | | 1 M | 48.0 | 96.8 | 0.11 | 0.43 | 0.13 | 1.03 |
| | 25° C. | 15 d | 49.6 | 100.0 | BDL | 0.10 | BDL | 0.30 |
| | | 1 M | 48.4 | 97.6 | 0.05 | 0.19 | BDL | 0.43 |
| | 5° C. | 1 M | 49.6 | 100.0 | BDL | 0.07 | BDL | 0.27 |
| BDM - 50 mg/mL Lipoic acid - 5 mg/mL PEG 400:PG (50:50) qs to 1 mL | | Initial | 50.2 | 100 | BDL | BDL | BDL | 0.21 |
| | 40° C. | 1 W | 49.9 | 99.4 | BDL | 0.15 | BDL | 0.30 |
| | | 15 d | 49.1 | 97.8 | 0.06 | 0.35 | BDL | 0.73 |
| | | 1 M | 49.0 | 97.6 | 0.09 | 0.90 | 0.25 | 1.82 |
| | 25° C. | 15 d | 49.9 | 99.4 | BDL | 0.12 | BDL | 0.32 |
| | | 1 M | 49.7 | 99.0 | BDL | 0.25 | BDL | 0.59 |
| | 5° C. | 1 M | 50.0 | 99.6 | BDL | 0.11 | BDL | 0.33 |
| BDM - 50 mg/mL Lipoic acid - 5 mg/mL PEG 400:PG (90:10) qs to 1 mL | | Initial | 50.8 | 100 | BDL | BDL | BDL | 0.21 |
| | 40° C. | 1 W | 50.4 | 99.2 | BDL | 0.11 | BDL | 0.30 |
| | | 15 d | 49.7 | 97.8 | 0.07 | 0.17 | BDL | 0.43 |
| | | 1 M | 49.7 | 97.8 | 0.13 | 0.27 | 0.09 | 0.84 |
| | 25° C. | 15 d | 50.8 | 100.0 | BDL | 0.10 | BDL | 0.26 |
| | | 1 M | 50.8 | 100.0 | 0.05 | 0.14 | BDL | 0.39 |
| | 5° C. | 1 M | 50.8 | 100.0 | BDL | 0.06 | BDL | 0.34 |

BDL = Below Detectable Limit

As shown in Table 5, bendamustine, when dissolved in certain mixtures of polyethylene glycol and propylene glycol and a stabilizing amount of lipoic acid, had substantially no increase in total degradants after a period of 1 month. The data presented in Table 5 translates to bendamustine-containing compositions having a shelf life of at least about 2 years when stored at temperatures between 5° C. and at 25° C.

Example 6

Bendamustine-containing compositions were prepared by dissolving bendamustine HCl to a concentration of 50 mg/ml in 90% polyethylene glycol 400 and 10% propylene glycol and α-lipoic acid was added as a stabilizing antioxidant as indicated in Table 6 below. The samples were maintained at 40° C., 25° C. and 5° C. and analyzed for drug content and impurity profile as indicated in Table 6 below. The results obtained are presented in Table 6.

TABLE 6

Stability of Bendamustine in 90% PEG 400, 10% PG and α-lipoic acid

| Formulation | Temp | Time Per. | Amt. mg/ml | % of Initial | 0.59 | 1.10 | 1.13 | 1.15 | 1.17 | 1.20 | 1.22 | 1.30 | % Total Imp. |
|---|---|---|---|---|---|---|---|---|---|---|---|---|---|
| BDM - | | Initial | 51.0 | 100 | 0.20 | 0.06 | <LD | <LD | <LD | <LD | <LD | <LD | 0.26 |
| 50 mg/mL | 40° C. | 1 M | 50.5 | 99.0 | 0.21 | 0.31 | 0.13 | 0.07 | 0.13 | 0.10 | <LD | <LD | 0.95 |
| α-lipoic | | 2 M | 49.7 | 97.5 | 0.22 | 0.71 | 0.28 | 0.14 | 0.12 | 0.21 | 0.12 | <LD | 2.02 |
| acid - | | 3 M | 48.7 | 95.5 | 0.22 | 1.01 | 0.45 | 0.21 | 0.14 | 0.37 | 0.16 | 0.05 | 2.96 |
| 10 mg/mL | 25° C. | 3 M | 50.5 | 99.0 | 0.20 | 0.36 | 0.07 | <LD | <LD | 0.10 | <LD | <LD | 0.73 |
| PEG | | 6 M | 50.4 | 98.8 | 0.22 | 0.60 | 0.17 | 0.06 | 0.06 | 0.09 | 0.10 | 0.08 | 1.44 |
| 400:PG | 5° C. | 6 M | 50.9 | 99.8 | 0.16 | 0.05 | <LD | <LD | <LD | <LD | <LD | <LD | 0.21 |
| (90:10) qs | | 12 M | 50.6 | 99.2 | 0.20 | 0.18 | <LD | <LD | <LD | <LD | <LD | <LD | 0.38 |
| to 1 mL | | | | | | | | | | | | | |
| BDM - | | Initial | 50.3 | 100 | 0.18 | <LD | <LD | <LD | <LD | <LD | <LD | <LD | 0.18 |
| 50 mg/mL | 40° C. | 1 M | 50.0 | 99.4 | 0.19 | 0.32 | 0.08 | 0.06 | 0.08 | 0.06 | 0.06 | <LD | 0.85 |
| α-lipoic | | 2 M | 49.8 | 99.0 | 0.19 | 0.65 | 0.21 | 0.12 | 0.13 | 0.23 | 0.14 | 0.06 | 1.85 |
| acid - | | 3 M | 49.5 | 98.4 | 0.15 | 0.89 | 0.37 | 0.17 | 0.13 | 0.32 | 0.10 | <LD | 2.40 |
| 15 mg/mL | | 6 M | 47.0 | 93.4 | 0.20 | 1.76 | 0.66 | 0.19 | 0.31 | 0.47 | 0.33 | 0.17 | 4.93 |
| PEG | 25° C. | 3 M | 50.0 | 99.4 | 0.20 | 0.35 | 0.08 | <LD | <LD | <LD | 0.11 | <LD | 0.79 |
| 400:PG | | 6 M | 49.5 | 98.4 | 0.19 | 0.58 | 0.15 | 0.06 | 0.07 | 0.09 | 0.08 | 0.10 | 1.38 |
| (90:10) qs | 5° C. | 6 M | 50.3 | 100 | 0.17 | 0.06 | <LD | <LD | <LD | <LD | <LD | <LD | 0.23 |
| to 1 mL | | 12 M | 50.2 | 99.8 | 0.19 | 0.15 | <LD | <LD | <LD | <LD | <LD | <LD | 0.34 |

<LD = Below Level of Detection

The data reported in Table 6 along with the data in Table 5 demonstrates that bendamustine solutions are stable when dissolved in mixtures of PEG and PG and 5-15 mg/mL α-lipoic acid. As shown in Table 6, bendamustine, when dissolved in combinations of polyethylene glycol and propylene glycol, in the presence of a stabilizing amount of lipoic acid, had less than 3% increase in total degradants after a period of 3 months at 40° C. Additionally, the same compounds had substantially no increase in total degradants after a period of 6-12 months at 5° C. and 25° C. The data corresponds to bendamustine solutions being stable under ambient or refrigerated storage conditions for well in excess of 2 years, and thus long term stable.

Example 7

Bendamustine-containing compositions were prepared by dissolving bendamustine HCl to a concentration of 50 mg/ml in 90% polyethylene glycol 400 and 10% propylene glycol. 2.5 mg/ml of thioglycerol was added as an antioxidizing agent. The samples were maintained at 40° C. and 25° C. and analyzed for drug content and impurity profile as indicated in Table 7 below. The results obtained are presented in Table 7.

The stability is similar to that of α-lipoic acid samples in Example 6 above. As shown in Table 7, bendamustine, when dissolved in a combination of polyethylene glycol and propylene glycol, and a stabilizing amount of thioglycerol, had less than 3% increase in total degradants after a period of 3 months at 40° C. Additionally, the same compounds had substantially no increase in total degradants after a period of 6 months at 25° C. The data reported supports the conclusion that these bendamustine solutions are stable under ambient or refrigerated storage conditions for about 2 years.

Example 8

Bendamustine-containing compositions were prepared by dissolving bendamustine HCl to a concentration of 50 mg/ml in 85% PEG 400 and 15% PG in the presence of 5 mg/ml of thioglycerol. The samples were maintained at 40° C. and 25° C. and analyzed for drug content and impurity profile as indicated in Table 8 below. The results obtained are presented in Table 8.

TABLE 7

Stability of Bendamustine in 90% PEG 400, 10% PG and Thioglycerol

| Formulation | Temp | Time Per. | Amt mg/ml | % of Initial | 0.15 | 0.37 | 1.10 | 1.13 | 1.15 | 1.17 | 1.18 | 1.20 | 1.22 | % Total Imp. |
|---|---|---|---|---|---|---|---|---|---|---|---|---|---|---|
| BDM - | | Initial | 50.3 | 100 | BDL | BDL | BDL | BDL | BDL | BDL | BDL | BDL | BDL | 0.00 |
| 50 mg/mL | 40° C. | 15 d | 50.2 | 99.8 | BDL | BDL | 0.18 | BDL | BDL | BDL | 0.05 | 0.08 | BDL | 0.31 |
| Thioglycerol | | 1 M | 49.9 | 99.2 | BDL | 0.12 | 0.32 | 0.07 | BDL | BDL | 0.09 | 0.08 | BDL | 0.75 |
| 2.5 mg/mL | | 2 M | 49.1 | 97.6 | BDL | 0.18 | 0.56 | 0.24 | 0.09 | 0.17 | 0.19 | 0.12 | 0.11 | 1.76 |
| PEG | | 3 M | 48.8 | 97.0 | BDL | 0.23 | 0.85 | 0.34 | 0.16 | 0.30 | 0.34 | 0.29 | 0.19 | 2.94 |
| 400:PG | 25° C. | 3 M | 49.9 | 99.2 | 0.06 | 0.12 | 0.23 | 0.07 | BDL | 0.06 | 0.07 | 0.06 | BDL | 0.67 |
| (90:10) qs | | 6 M | 49.3 | 98.0 | BDL | 0.23 | 0.53 | 0.22 | 0.11 | BDL | 0.21 | 0.22 | 0.20 | 2.07 |
| to 1 mL | | | | | | | | | | | | | | |

BDL = Below Detectable Limit

TABLE 8

Stability of Bendamustine in 85% PEG 400, 15% PG and Thioglycerol

| Formulation | Temp. | Time Period | Content (mg/mL) | % of Initial | % Total Imp. |
|---|---|---|---|---|---|
| BDM—50 mg/mL | Initial | | 51.5 | 100 | 0.12 |
| Thioglycerol—5 mg/mL | 40° C. | 1 M | 50.4 | 97.9 | 1.18 |
| PEG 400:PG (85:15) qs to 1 mL | 25° C. | 1 M | 51.4 | 99.8 | 0.41 |
| | | 3 M | 50.4 | 97.9 | 1.21 |
| | 5° C. | 3 M | 51.0 | 99.0 | 0.26 |

The stability is similar to that of thioglycerol samples in Example 7 above. As reported in Table 8, total impurities did not exceed 2% at 40° C. or 25° C. storage over one month, or at 25° C. and 5° C. storage after three months. The data reported in Table 8 supports the conclusion that these bendamustine solutions are stable under ambient or refrigerated storage conditions for at least about 2 years if not longer.

We claim:

1. A ready to use liquid bendamustine-containing composition comprising
bendamustine, or a pharmaceutically acceptable salt thereof, wherein the bendamustine concentration in the composition is from about 10 mg/mL to about 100 mg/mL;
polyethylene glycol; and
a stabilizing amount of an antioxidant;
the composition having less than about 5% peak area response of total impurities resulting from the degradation of the bendamustine, as determined by HPLC as a wavelength of 223 nm after at least 15 months at a temperature of from about 5° C. to about 25° C.

2. The ready to use liquid bendamustine-containing composition of claim 1, wherein the antioxidant is lipoic acid, thioglycerol, propyl gallate, methionine, cysteine, a metabisulfite, sodium formaldehyde sulfoxylate, a phenol-containing aromatic compound, a phenol-containing aliphatic compound, dihydrolipoic acid, or a mixture thereof.

3. The ready to use liquid bendamustine-containing composition of claim 1, having less than about 5% peak area response of total impurities resulting from the degradation of the bendamustine, as determined by HPLC as a wavelength of 223 nm after at least 15 months at a temperature of about 5° C.

4. The ready to use liquid bendamustine-containing composition of claim 1, having less than about 5% peak area response of total impurities resulting from the degradation of the bendamustine, as determined by HPLC as a wavelength of 223 nm after at least 15 months at a temperature of about 25° C.

5. The ready to use liquid bendamustine-containing composition of claim 1, wherein the bendamustine concentration is from about 20 mg/mL to about 60 mg/mL.

6. The ready to use liquid bendamustine-containing composition of claim 1, wherein the bendamustine concentration is about 25 mg/mL.

7. The ready to use liquid bendamustine-containing composition of claim 1, comprising bendamustine hydrochloride.

8. A method of treating cancer in a mammal, comprising administering an effective amount of the ready to use liquid bendamustine-containing composition of claim 1 to the mammal.

9. The method of claim 8, wherein the cancer is leukemia.

10. The method of claim 8, wherein the cancer is Hodgkin's disease.

11. The method of claim 8, wherein the antioxidant is lipoic acid, thioglycerol, propyl gallate, methionine, cysteine, a metabisulfite, sodium formaldehyde sulfoxylate, a phenol-containing aromatic compound, a phenol-containing aliphatic compound, dihydrolipoic acid, or a mixture thereof.

12. The method of claim 8, wherein the ready to use liquid bendamustine-containing composition has less than about 5% peak area response of total impurities resulting from the degradation of the bendamustine, as determined by HPLC as a wavelength of 223 nm after at least 15 months at a temperature of about 5° C.

13. The method of claim 8, wherein the ready to use liquid bendamustine-containing composition has less than about 5% peak area response of total impurities resulting from the degradation of the bendamustine, as determined by HPLC as a wavelength of 223 nm after at least 15 months at a temperature of about 25° C.

14. The method of claim 8, wherein the bendamustine concentration in the ready to use liquid bendamustine-containing composition is from about 20 mg/mL to about 60 mg/mL.

15. The method of claim 8, wherein the bendamustine concentration in the ready to use liquid bendamustine-containing composition is about 25 mg/mL.

16. The method of claim 8, wherein the ready to use liquid bendamustine-containing composition comprises bendamustine hydrochloride.

* * * * *